(12) United States Patent
Goettel et al.

(10) Patent No.: US 7,455,697 B2
(45) Date of Patent: Nov. 25, 2008

(54) (3,5-DIAMINOPHENYL)(2,4-DIHYDROXY-PHENYL)METHANONE AND THE ACID ADDUCTS THEREOF, METHOD FOR THEIR PREPARATION AND USE OF THESE COMPOUNDS FOR DYEING FIBERS

(75) Inventors: Otto Goettel, Marly (CH); Andre Hayoz, Senedes (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 183 days.

(21) Appl. No.: 10/589,179

(22) PCT Filed: Dec. 2, 2004

(86) PCT No.: PCT/EP2004/013704

§ 371 (c)(1),
(2), (4) Date: Aug. 11, 2006

(87) PCT Pub. No.: WO2005/080315

PCT Pub. Date: Sep. 1, 2005

(65) Prior Publication Data

US 2007/0180629 A1    Aug. 9, 2007

(30) Foreign Application Priority Data

Feb. 24, 2004  (DE) .................. 10 2004 008 918

(51) Int. Cl.
*A61Q 5/10* (2006.01)
(52) U.S. Cl. .................. 8/405; 8/406; 8/410; 8/411; 8/421; 8/424; 8/435

(58) Field of Classification Search .................. 8/405, 8/406, 410, 411, 421, 424, 435
See application file for complete search history.

(56) References Cited

U.S. PATENT DOCUMENTS 5,576,142 A * 11/1996 Neumann et al. ........... 430/269
2004/0147515 A1    7/2004 Umbricht et al.

FOREIGN PATENT DOCUMENTS

DE    101 28 472    12/2002
DE    102 17 270    11/2003

OTHER PUBLICATIONS

STIC Search Report dated Mar. 12, 2008.*

* cited by examiner

*Primary Examiner*—Eisa B Elhilo
(74) *Attorney, Agent, or Firm*—Michael J. Striker

(57) ABSTRACT

The object of the present invention are (3,5-diaminophenyl)(2,4-dihydroxyphenyl)methanone and the acid adducts thereof of formula (I), with $0 \leq n \leq 2$ and HX denoting an inor-ganic or organic acid,

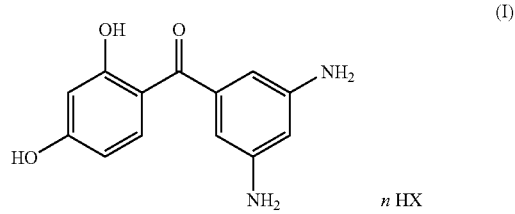

the colorant containing these compounds and a method for producing the compounds of formula (I).

10 Claims, No Drawings

(3,5-DIAMINOPHENYL)(2,4-DIHYDROXY-PHENYL)METHANONE AND THE ACID ADDUCTS THEREOF, METHOD FOR THEIR PREPARATION AND USE OF THESE COMPOUNDS FOR DYEING FIBERS

FIELD OF THE INVENTION

The present invention has for an object (3,5-diaminophenyl)(2,4-dihydroxyphenyl)metha-none and the acid adducts thereof, a method for their preparation and the use of these compounds for dyeing fibers.

BACKGROUND OF THE INVENTION

In the field of hair dyeing, oxidation dyes have attained substantial importance. The dyeing in this case occurs by reaction of certain developers with certain couplers in the presence of an oxidant. Now as before, colorants that cover the range of natural colors are of particular interest. Until now, the important range of natural shades, particularly the darker nuances, could be covered only by use of complicated mixtures of several different developers and couplers. Normally, combinations of para-phenylenediamines with re-sorcinols, m-aminophenols and m-phenylenediamines were used for this purpose. At the present time, for several reasons, the derivatives of these compounds and not the parent compounds themselves are used in most cases. Because of the complicated compositions required to obtain medium to the dark brown shades, it was desirable to have components capable of producing brown shades without the need for complicated compositions of numerous individual dye components, a 1:1 composition of a single developer and a single coupler being of particular interest.

SUMMARY OF THE INVENTION

Our goal was therefore to find a coupler component which together with appropriate developers would produce brown shades and colorations showing high stability under everyday conditions, for example frequent washing. Moreover, the undesirable color changes resulting from a premature fading of individual dyes in complicated compositions was to be prevented.

DETAILED DESCRIPTION OF THE INVENTION

Surprisingly, we have now found that the coupler of formula (I) and the salts thereof meet these requirements in outstanding manner.

The present invention therefore has for an object (3,5-diaminophenyl)(2,4-dihydroxyphe-nyl)methanone and the acid adducts thereof of formula (I), with $0 \leq n \leq 2$ and HX denoting an inorganic or organic acid.

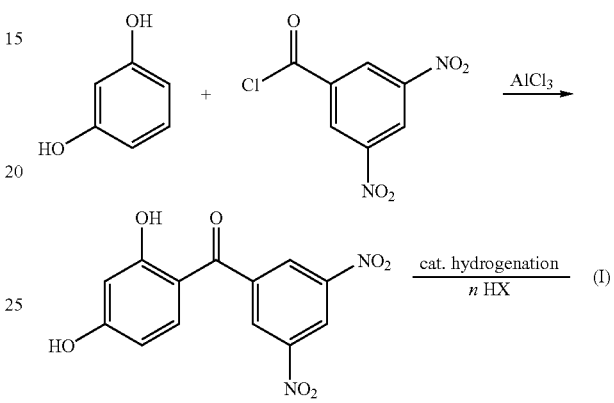

Suitable inorganic or organic acids are hydrochloric acid, sulfuric acid, phosphoric acid, citric acid and tartaric acid, among which hydrochloric acid and sulfuric acid are particularly preferred.

The compounds of formula (I) can be prepared according to Scheme I from 3,5-dinitrobenzoyl chloride and resorcinol under Friedel-Crafts conditions. The intermediate product is catalytically hydrogenated to give the end product of formula (I) which can be isolated either as the free base or as the acid adduct.

Scheme 1: Preparation of the compound of formula (I)

The invention also has for an object the use of the compounds of formula (I) alone or in combination with certain developers and couplers for the oxidative dyeing of synthetic or natural fibrous materials. Suitable among the natural fibrous materials are, for example, keratinic fibers, for example wool or hair and particularly human hair.

The compounds of the para-phenylenediamine, para-aminophenol and 4,5-diaminopyrazole type which are eminently suited as color developers for combination in oxidative formulations are the following, compounds which, of course, are also usable in the form of acid adducts. In particular, such compounds include 1,4-diaminobenzene (p-phenylenediamine), 1,4-diamino-2-methylbenzene (p-toluylenediamine), 1,4-diamino-2,6-dimethylbenzene, 1,4-diamino-2,5-dimethylbenzene, 1,4-diamino-2,3-dimethylbenzene, 2-chloro-1,4-diaminobenzene, 4-phenylaminoaniline, 4-dimethylaminoaniline, 4-diethylaminoaniline, 4-[di(2-hydroxyethyl)amino]aniline, 1,4-diamino-2-methoxymethylbenzene, 1,4-diamino-2-aminomethylbenzene, 1,4-diamino-2-phenylbenzene, 4-[(2-methoxyethyl)amino]aniline, 4-[(3-hydroxypropyl)amino]aniline, 1,4-diamino-2-(2-hydroxyethyl)benzene, 1,4-diamino-2-(1-methylethyl)benzene, 1,3-bis[(4-aminophenyl)-(2-hydroxyethyl)amino]-2-propanol, 1,8-bis(2,5-diaminophenoxy)-3,6-dioxaoctane, 4-aminophenol, 4-amino-3-methylphenol, 4-methylaminophenol, 4-amino-2-(aminomethyl)phenol, 4-amino-2-[(2-hydroxyethyl)amino]methylphenol, 4-amino-2-(methoxymethyl)phenol, 4-amino-2-(2-hydroxyethyl)phenyl, 5-aminosalicylic acid, 2,5-diaminopyridine, 2,4,5,6-tetraaminopyridine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 4,5-diamino-1-pentyl-1H-pyrazole, 4,5-diamino-3-methyl-1-phenyl-1H-pyrazole, 4,5-diamino-1-(2-hydroxyethyl)-3-methyl-1H-pyrazole, 1,2-bis(4,5-diamino- 1H-pyrazol-1-yl)-ethane, 1,4-bis-(4,5-diaminopyrazol-1-yl-methyl)benzene, 4,5-diamino-1-(2-methylphenyl)-1H-pyrazole, 4,5-diamino-1-(3-methylphenyl)-1H-pyrazole, 4,5-diamino-1-(4-methylphenyl)-1H-pyrazole, 4,5-diamino-1-(2,4-dimethylphenyl)-1H-pyrazole, 4,5-diamino-1-(2,5-dimethylphenyl)-1H-pyrazole, 4,5-diamino-1-(2-ethylphenyl)-1H-pyrazole, 4,5-diamino-1-(4-isopropylphenyl)-1H-pyrazole, 4,5-diamino-1-(4-methoxyphenyl)-1H-pyrazole, 1-(4-aminophenyl)4,5-diamino-1H-pyrazole, 1-(4-chlorophenyl)4,5-diamino-1H-pyrazole, 4,5-diamino-1-(2-pyridinyl)-1H-pyrazole, 2-aminophenol, 2-amino-6-methylphenol and 2-amino-5-methylphenol and the salts thereof.

Couplers which in combination with the compounds of formula (I) of the invention can be used to create certain color shades are the following compounds: N-(3-dimethylaminophenyl)urea, 2,6-diaminopyridine, 2-amino-4-[(2-hydroxyethyl)amino]-anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxy-ethoxy)benzene, 2,4-diamino-1-(3-hydroxypropoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di[2,4-diaminophenoxy)propane, di[2,4-diaminophenoxy)-methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-2-methylphenol, 3-[(2-hydroxyethyl)amino]-phenol, 3-[(2-methoxyethyl)amino]phenol, 5-amino-2-ethylphenol, 2-(4-amino-3-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxybenzene, 1-chloro-2,4-dihydroxybenzene, 1-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione as well as the salts thereof.

For dyeing, the afore-described compounds of formula (I) are applied in a suitable dye carrier composition.

The present invention therefore also has for an object a ready-to-use agent for oxidative dyeing of keratin fibers, particularly hair, which is prepared just before use by mixing a dye carrier composition with an oxidant and is characterized in that the dye carrier composition contains at least one compound of formula (I).

The colorant of the invention contains the compounds of formula (I) preferably in an amount (based on the dye carrier composition) from 0.01 to 10 weight percent and particularly from 0.1 to 6 weight percent.

Besides the compounds of formula (I) and the afore-said developers and couplers, the colorant of the invention can also contain direct dyes from the group of anionic, cationic or neutral dyes. The preferred anionic dyes are, for example: 6-hydroxy-5-[(4-sulfophenyl)azo]-2-naphthalenesulfonic acid disodium salt (C. I. 15 985; Food Yellow No. 3; FD&C Yellow No. 6), 2,4-dinitro-1-naphthol-7-sulfonic acid disodium salt (C.I. 10316; Acid Yellow No. 1; Food Yellow No. 1), 2-(indan-1,3-dion-2-yl)quinoline-x,x-sulfonic acid (mixture of mono- and disulfonic acid) (C.I. 47005; D&C Yellow No. 10; Food Yellow No. 13; Acid Yellow No. 3), 5-hydroxy-1-(4-sulfophenyl)-4-[(4-sulfophenyl)azo]pyrazole-3-carboxylic acid trisodium salt (C.I. 19140; Food Yellow No. 4; Acid Yellow No. 23), 9-(2-carboxyphenyl)-6-hydroxy-3H-xanthen-3-one (C.I. 45350; Acid Yellow No. 73; D&C Yellow No. 8), 5-[(2,4-dinitrophenyl)amino]-2-phenylamino-benzenesulfonic acid sodium salt (C.I. 10385; Acid Orange No. 3), 4-[(2,4-dihydroxyphenyl)azo]benzenesulfonic acid monosodium salt (C.I. 14270; Acid Orange No. 6), 4-[(2-hydroxynaphth-1-yl)-azo]benzenesulfonic acid sodium salt (C.I. 15510; Acid Orange No. 7), 4-[(2,4-dihydroxy-3-[(2,4-dimethylphenyl)azo]phenyl)azo]benzenesulfonic acid sodium salt (C.I. 20170; Acid Orange No. 24), 4-hydroxy-3-[(4-sulfonaphth-1-yl)azo]-1-naphthalenesulfonic acid diso-dium salt (C.I. 14720; Acid Red No. 14), 6-hydroxy-5-[(4-sulfonaphth-1-yl)azo]-2,4-naphthalenedisulfonic acid trisodium salt (C.I. 16255; Ponceau 4R; Acid Red No. 18), 3-hydroxy-4-[(4-sulfonaphth-1-yl)azo]-2,7-naphthalenedisulfonic acid trisodium salt (C.I. 16185; Acid Red No. 27), 8-amino-1-hydroxy-2-(phenylazo)-3,6-naphthalenedisulfonic acid disodium salt (C.I. 17200, Acid Red No. 33), 5-(acetylamino)-4-hydroxy-3-[(2-methylphenyl)azo]-2,7-naphthalenedisulfonic acid disodium salt (C.I. 18065; Acid Red No. 35), 2-(3-hydroxy-2,4,5,7-tetraiodod-ibenzopyran-6-on-9-yl)benzoic acid disodium salt (C.I. 45430; Acid Red No. 51), N-[6-(diethylamino)-9-(2,4-disulfophenyl)-3H-xanthen-3-yli-dene]-N-ethylethanaminium hydroxide, inner salt, sodium salt (C.I. 45100; Acid Red No. 52), 8-{[4-(phenylazo)phenyl]azo}-7-naphthol-1,3-disulfonic acid disodium salt (C.I. 27290; Acid Red No. 73), 2',4',5',7'-tetrabromo-3',6'-dihydroxyspiro{isobenzofuran-1(3H),9'-[9H]xanthen}-3-one disodium salt (C.I. 45380; Acid Red No. 87), 2',4',5',7'-tetrabromo-4,5,6,7-tetrachloro-3',6'-dihydroxyspiro{isobenzofuran-1(3H),9'-[9H]xanthen}-3-one disodium salt (C.I. 45410; Acid Red No. 92), 3',6'-dihydroxy-4',5'-diiodospiro[isobenzofuran-1(3H),9'-(9H)xanthen]-3-one disodium salt (C. I. 45425; Acid Red No. 95), (2-sulfophenyl)-di[4-(ethyl((4-sulfophenyl)methyl)amino)phenyl]carbenium disodium salt, betaine (C.I. 42 090; Acid Blue No. 9; FD&C Blue No. 1), 1,4-bis[(2-sulfo-4-methylphenyl)amino]-9,10-anthraquinone disodium salt (C.I. 61570; Acid Green No. 25), bis[4-(dimethylamino)-phenyl]-(3,7-disulfo-2-hydroxynaphth-1-yl)carbenium inner salt, monosodium salt (C.I. 44090; Food Green No. 4; Acid Green No. 50), bis[4-(diethylamino)phenyl](2,4-disulfophenyl)carbenium inner salt, sodium salt (2:1) (C.I. 42045; Food Blue No. 3; Acid Blue No. 1), bis[4-(diethylamino)phenyl](5-hydroxy-2,4-disulfophenyl)carbenium inner salt, calcium salt (2:1) (C.I. 42051; Acid Blue No. 3), 1-amino-4-(cyclohexylamino)-9,10-anthraquinone-2-sulfonic acid sodium salt (C.I. 62045; Acid Blue No. 62), 2-(1,3-dihydro-3-keto-5-sulfo-2H-indol-2-ylidene)-2,3-dihydro-3-keto-1H-indole-5-sulfonic acid disodium salt (C.I. 73015; Acid Blue No. 74), 9-(2-carboxyphenyl)-3-[(2-methylphenyl)amino]-6-[(2-methyl-4-sulfophenyl)amino]xanthylium inner salt, monosodium salt (C.I. 45190; Acid Vio-let No. 9), 1-hydroxy-4-[(4-methyl-2-sulfophenyl)amino]-9,10-anthraquinone sodium salt (C.I. 60730; D&C Violet No. 2; Acid Violet No. 43), bis{3-nitro-4-[(4-phenylamino)-3-sulfophenylamino]phenyl} sulfone (C.I. 10410; Acid Brown No. 13), 5-amino-4-hydroxy-6-[(4-nitrophenyl)azo]-3-(phenylazo)-2,7-naphthalenedisulfonic acid disodium salt (C.I. 20470; Acid Black No. 1), 3-hydroxy-4-[(2-hydroxynaphth-1-yl)azo]-7-nitro-1-naphthalenesulfonic acid chromium complex (3:2) (C.I. 15711; Acid Black No. 52), 3-[(2,4-dimethyl-5-sulfo-phenyl)azo]-4-hydroxy-1-naphthalenesulfonic acid disodium salt (C.I. 14700; Food Red No. 1; Ponceau SX; FD&C Red No. 4), 4-(acetylamino)-5-hydroxy-6-[(7-sulfo-4-[(4-sulfophenyl)azo]naphth-1-yl)azo]-1,7-naphthalenedisulfonic acid tetrasodium salt (C.I. 28440; Food Black No. 1) and 3-hydroxy-4-(3-methyl-5-keto-1-phenyl-4,5-dihydro-1H-pyrazol-4-ylazo)naphthalene-1-sulfonic acid sodium salt chromium complex (Acid Red No. 195).

The following nonionic dyes are particularly well suited for better color balancing and creation of special color shades: 1-amino-2-[(2-hydroxyethyl)amino]-5-nitrobenzene (HC Yellow No. 5), 1-(2-hydroxyethoxy)-2-[(2-hydroxyethyl)amino]-2-nitrobenzene (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No. 9), 1-[(2-ureidoethyl)amino]-4-nitrobenzene, 4-[(2,3-dihydroxypropyl)-amino]-3-nitro-1-trifluoromethylbenzene (HC Yellow No. 6), 1-chloro-2,4-bis-[(2-hydroxy-ethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 1-amino-4-[(2-hydroxyethyl)amino]-2-nitrobenzene (HC Red No. 7), 2-amino-4,6-dinitrophenol, 2-ethylamino-4,6-dinitrophenol, 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-amino-3-nitrophenol, 4-[(2-hydroxyethyl)amino]-3-nitrophenol, 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)amino]4,6-dinitrophenol, 4-ethylamino-3-nitrobenzoic acid, 2-[(4-amino-2-nitrophenyl)amino]benzoic acid, 2-chloro-6-methylamino-4-nitrophenol, 2-chloro-6-[(2-hydroxyethyl)amino]4-nitrophenol, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 1,2,3,4-tetrahydro-6-nitroquinoxaline, 7-amino-3,4-dihydro-6-nitro-2H-1,4-benzoxazine (HC Red No. 14), 1,4-bis[(2-hydroxyethyl)amino]-2-nitrobenzene, 1-(2-hydroxyethyl)amino-2-nitro-4-[di(2-hydroxyethyl)amino]benzene (HC Blue No. 2), 1-amino-3-methyl-4-[(2-hydroxyethyl)amino]-6-nitrobenzene (Violet No. 1), 4-[ethyl-(2-hydroxyethyl)amino]-1-[(2-hydroxyethyl)amino]-2-nitrobenzene hydrochloride (HC Blue No. 12), 4-[di(2-hydroxyethyl)amino]-1-[(2-methoxyethyl)amino]-2-nitrobenzene (HC Blue No. 11), 1-[(2,3-dihydroxypropyl)amino-4-[methyl-(2-hydroxyethyl)amino]-2-nitrobenzene (HC Blue No. 10), 1-[(2,3-dihydroxypropyl)amino]4-[ethyl-(2-hydroxyethyl)amino]-2-nitrobenzene hydrochloride (HC Blue No. 9), 1-(3-hydroxypropylamino)-4-[di(2-hydroxyethyl)-amino]-2-nitrobenzene (HC Violet No. 2), 1-methylamino-4-[methyl-(2,3-dihydroxypropyl)amino]-2-nitrobenzene (HC Blue No. 6), 2-[(4-amino-2-nitrophenyl)amino]-5-dimethylaminobenzoic acid (HC Blue No. 13), 1,4-di-[(2,3-dihydroxypropyl)amino]-9,10-anthraquinone, 1-[(2-hydroxyethyl)amino]4-methylamino-9,10-anthraquinone (C.I. 61 505, Disperse Blue No. 3), 2-[(2-aminoethyl)amino]-9,10-anthraquinone (HC Orange No. 5), 1-hydroxy-4-[(4-methyl-2-sulfophenyl)amino-9,10-anthraquinone, 1-[(3-aminopropyl)amino]-4-methylamino-9,10-anthraquinone (HC Blue No. 8), 1-[(3-aminopropyl)amino]-9,10-anthraquinone (HC Red No. 8), 1,4-diamino-2-methoxy-9,10-anthraquinone (C.I. 62015, Disperse Red No. 11, Solvent Violet No. 26), 1,4-dihydroxy-5,8-bis[(2-hydroxyethyl)amino]-9,10-anthraquinone (C.I. 62500, Disperse Blue No. 7, Solvent Blue No. 69), 1-[di(2-hydroxyethyl)amino]-3-methyl-4-[(4-nitrophenyl(azo]benzene (C.I. 11210; Disperse Red No. 17), 4-[(4-aminophenyl)azo]-1-[di(2-hydroxyethyl)amino]3-methylbenzene (HC Yellow No. 7), 2,6-diamino-3-[(pyridin-3-yl)azo]pyridine and 2-[(4-acetylamino)phenyl]azo-4-methylphenol (C.I. 11855; Disperse Yellow No. 3). Particularly well suited from the group of direct dyes are also 2-amino-4,6-dinitrophenol, 2-ethylamino-4,6-dinitrophenol, 2-[(2-hydroxyethyl)amino] 4,6-dinitrophenol and the dyes of general formula (II)

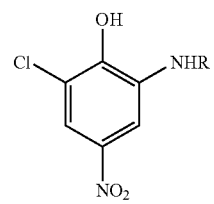

Formula (II)

wherein R stands for hydrogen, methyl, ethyl or hydroxyethyl.

The total amount of oxidation dye precursors (based on the dye carrier composition) is from 0.01 to 10 weight percent and particularly from 0.2 to 6 weight percent.

The total amount of direct dyes in the dye carrier composition is between 0.1 and 10 weight percent, a total amount of 0.1 to 5 weight percent being preferred.

Moreover, the dye carrier composition can also contain antioxidants (for example sodium sulfite and/or ascorbic acid), perfume oils, complexing agents, wetting agents, emulsifiers, penetrants, buffering systems, preservatives, thickeners, hair-care agents and other cosmetic additives.

The dye carrier composition and the ready-to-use oxidation hair colorant can be in the form of, for example, a solution, particularly an aqueous or aqueous-alcoholic solution. A particularly preferred form, however, is a cream, a gel and an emulsion. Such compositions consist of a mixture of the dye components with additives commonly used in such preparations.

Common additives for solutions, creams, emulsions and gels are, for example, solvents such as water, the lower aliphatic alcohols, for example ethanol, n-propanol and isopropanol, or glycols such as glycerol and 1,2-propylene glycol, furthermore wetting agents and emulsifiers from the classes of anionic, cationic, amphoteric or nonionic surface-active substances, such as the fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty alkanolamides, ethoxylated fatty esters, furthermore thickeners such as the higher fatty alcohols, starch and cellulose derivatives, moreover vaseline, paraffin oil and fatty acids as well as hair-care agents such as cationic resins, lanolin derivatives, cholesterol, pantothenic acid and betaine. The said constituents are used in amounts normally employed for such purposes. Based on the dye carrier composition, the wetting agents and emulsifiers, for example, are used at a concentration of about 0.5 to 30 weight percent, the thickeners in an amount from about 0.1 to 25 weight percent and the hair-care agents at a concentration of about 0.1 to 5 weight percent.

The ready-to-use hair colorant of the invention is prepared by mixing the dye carrier composition with a liquid oxidant just before use.

Suitable oxidants are mainly hydrogen peroxide and the compounds of addition thereof to urea, melamine or sodium bromate in the form of a 1 to 12% and preferably 6% aqueous solution, hydrogen peroxide being particularly preferred.

The dye carrier composition and the oxidant are mixed with one another in a weight ratio from 5:1 to 1:3, a weight ratio of 1:1 to 1:2 being particularly preferred.

When the preferably alkaline dye carrier composition is mixed with the usually acidic oxidant, the pH of the ready-to-use hair colorant assumes a value that is determined by the amounts of alkaline materials in the dye carrier composition and by the amounts of acids in the oxidant as well as by the mixing ratio. The pH of the ready-to-use hair colorant ranges from 3 to 11 and preferably from 6 to 10.5.

An organic or inorganic acid, for example phosphoric acid, ascorbic acid and lactic acid, or an alkaline material such as monoethanolamine, triethanolamine, 2-amino-2-methyl-1-propanol, ammonia, sodium hydroxide, potassium hydroxide or tris(hydroxymethyl)aminomethane can be used to adjust the pH of the dye carrier composition and of the oxidant.

After the afore-described dye carrier composition has been mixed with the oxidant, an amount of the ready-to-use oxidation hair colorant sufficient for hair coloring, in general about 60 to 200 g depending on the hair fullness, is applied to the hair.

The hair colorant is allowed to act on the hair for about 10 to 45 min at about 10 to 50° C., preferably 30 min at 40° C., after which the hair is rinsed with water. Following this rinsing, the hair is optionally washed with a shampoo and possibly post-rinsed with a dilute weak organic acid, for example citric acid or tartaric acid. The hair is then dried.

The following examples will explain the subject matter of the invention in greater detail without, however, limiting it to these examples.

EXAMPLES

Example 1

Preparation of (3,5-diaminophenyl)(2,4-dihydroxyphenyl)methanone

Step 1: (2,4-Dihydroxyphenyl)(3,5-dinitrophenyl)methanone 17.6 g (160 mmol) of resorcinol was dissolved in 80 mL of sulfolane (tetrahydrothiophene 1,1-dioxide). Then, 21.6 g (160 mmol) of aluminum chloride was added. At 60° C., 34 g (148 mmol) of 3,5-dinitrobenzoyl chloride was added portionwise over a period of 20 min which resulted in an evolution of gaseous hydrogen chloride. At the end of the addition, the mixture was heated at 90° C. for an additional 4 hours. The reaction mixture was then cooled and to it was carefully added 320 mL of 5% hydrochloric acid. The resulting precipitate was separated by decantation of the supernatant solution, 400 mL of ethanol was added, and crystallization was brought about by stirring at room temperature. The crystals were suction-filtered off and dried under vacuum. This gave 40 g of a yellowish product.

$^1$H-NMR (DMSO-d$_6$): δ=11.32 ppm (s, 1H); 10.78 ppm (s, 1H); 9.98 ppm (t, $^4J_{HH}$=2.1 Hz, 1H); 8.73 ppm (d, $^4J_{HH}$=2.1 Hz, 2H); 7.44 ppm (dd, $^3J_{HH}$=8.1 Hz, $^4J_{HH}$=0.9 Hz, 1H); 6.43 ppm (d, $^4J_{HH}$=2.1 Hz, 1H); 6.40 ppm (s, 1H).

Elemental analysis: $C_{13}H_8N_2O_7$; mol. wt.=304.21

|  | % C | % H | % N |
|---|---|---|---|
| Calculated: | 51.33 | 2.65 | 9.21 |
| Found: | 50.95 | 2.68 | 8.87 |

Step 2

(3,5-Diaminophenyl)(2,4-dihydroxyphenyl)methanone Dihydrochloride 25.0 g (82 mmol) of the product from Step 1 was hydrogenated in 300 mL of ethanol in the presence of 2.5 g of Pd/C, 10%, under 9 bar of hydrogen pressure. After 6 hours, the catalyst was filtered off, 100 mL of 32% hydrochloric acid was added to the filtrate and the solution was concentrated in a rotary evaporator. This caused gradual crystallization of the product and the formation of a crystalline slurry. To complete the crystallization, the slurry was cooled in an ice bath for an additional hour. The mixture was suction-filtered and the filter cake was washed with ethyl acetate and then dried at 40° C. under vacuum. This gave 18.3 g (70% of the theoretical) of a beige-colored product.

$^1$H-NMR (DMSO-d$_6$): δ=8.60 (s broad, 8H); 7.38 (d, $^3J_{HH}$=9.3 Hz, 1H); 7.01 (signal overlap, 3H); 6.42 ppm (signal overlap, 2H).

$^{13}$H-NMR (DMSO-d$_6$): δ=196.0 (CO); 165.0 (C—OH); 163.7 (C—OH); 140.1 (2 C-NH$_2$); 136.7 (C); 134.7 (CH); 117.9 (2 CH); 116.5 (CH); 112.5 (C); 108.3 (CH); 102.8 ppm (CH).

Elemental analysis: $C_{13}H_{12}N_2O_3$2 HCl; mol. wt.=317.17; 1.3% of water of crystallization

|  | % C | % H | % N | % Cl |
|---|---|---|---|---|
| Calculated: | 48.84 | 5.16 | 8.76 | 21.07 |
| Found: | 48.74 | 5.08 | 8.58 | 20.91 |

Step 3

(3,5-Diaminophenyl)(2,4-dihydroxyphenyl)methanone 1 g (3.1 mmol) of (3,5-diaminophenyl)(2,4-dihydroxyphenyl)methanone dihydrochloride was dissolved in 30 mL of water and neutralized by addition of a saturated sodium hydrogen carbonate solution. This produced a yellowish precipitate which was suction-filtered off. The filter cake was washed with a small amount of cold water and dried at 40° C. under vacuum. This gave 0.6 g (78% of the theoretical) of a yellowish powder.

FAB-MS: 245 [M+1]$^+$, 100% $^1$H-NMR (DMSO-$d_6$: δ=12.52 (s, 1H); 10.66 (s, 1H); 7.52 (d, $^3J_{HH}$=8.7 Hz, 1H); 6.35 (signal overlap, 2H); 6.02 (m centered, 3H); 5.05 ppm (s broadened, 5H).

Example 2

Hair Colorant

Dye Carrier Composition

| | |
|---|---|
| 10.0 g | of ethanol |
| 10.0 g | of sodium lauryl ether sulfate, 28% aqueous solution |
| 10.0 g | of ammonia, 25% aqueous solution |
| 0.3 g | of ascorbic acid |
| 0.4 g | of (3,5-diaminophenyl)(2,4-dihydroxyphenyl)methanone dihydrochloride |
| X g | of developer as per Table 1 |
| to 100.00 g | water |

Just before use, 100 g of the foregoing dye carrier composition was mixed with 100 g of a 6% aqueous hydrogen peroxide solution and a required amount of the resulting ready-to-use oxidation hair colorant was applied to hair. After an exposure time of 30 min at 40 ° C., the hair was washed with a shampoo, rinsed with water and dried. This gave the color shades shown in Table 1.

TABLE 1

| Example No. | Amount | Developer | Color Shade |
|---|---|---|---|
| 2a | 0.28 g | 2,5-diaminotoluene sulfate | light-brown |
| 2b | 0.32 g | 1,4-diamino-2-(2-hydroxyethyl)benzene sulfate (1:1) | light-brown |
| 2c | 0.16 g | 4-amino-3-methylphenol | ash-blond |
| 2d | 0.30 g | 4,5-diamino-1-(2-hydroxyethyl)-1H-pyrazole sulfate (1:1) | red-violet |
| 2e | 0.37 g | 4-[di(2-hydroxyethyl)amino]aniline sulfate(1:1) | medium brown |
| 2f | 0.14 g<br>0.15 g | 2,5-diaminotoluene sulfate<br>4,5-diamino-1-(2-hydroxyethyl)-1H-pyrazole sulfate (1:1) | wine-red |

Example 3

Hair-Dyeing Cream

| | |
|---|---|
| 15.00 g | of cetylstearyl alcohol (50/50) |
| 5.00 g | of glycerol monostearate |
| 2.00 g | of Cocamide DEA |
| 10.00 g | of sodium lauryl ether sulfate, 28% aqueous solution |
| 0.30 g | of ascorbic acid |
| 0.40 g | of sodium sulfite |
| 4.50 g | of ammonia, 25% aqueous solution |
| 0.55 g | of 2,5-diaminotoluene sulfate |
| 0.79 g | of (3,5-Diaminophenyl)(2,4-dihydroxyphenyl)methanone dihydrochloride |
| to 100.00 g | water, demineralized |

The cream had a pH of 10.2.

Just before use, 100 g of the foregoing dye carrier composition was mixed with 100 g of a 6% aqueous hydrogen peroxide emulsion and a required amount of the resulting ready-to-use oxidation hair colorant was applied to hair. After an exposure time of 30 minutes at 40° C., the hair was washed with a shampoo, rinsed with water and dried. The shades obtained on different hair types are shown in Table 2.

TABLE 2

| Hair Type | Shade |
|---|---|
| bleached hair | medium to dark brown |
| human hair with 50% gray content | medium brown, very good gray coverage |
| human hair, shade depth 7/0 | medium brown |

Unless otherwise indicated, all percentages given in the present patent application are by weight.

The invention claimed is:

1. (3,5-Diaminophenyl)(2,4-dihydroxyphenyl)methanone and the acid adducts thereof of formula (I), with $0 \leq n \leq 2$ and HX denoting an inorganic or organic acid.

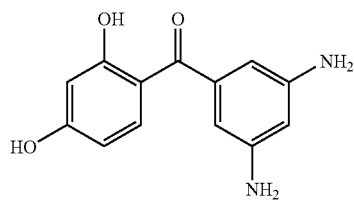

(I)

$n$ HX

2. Compound as defined in claim 1, characterized in that the HX acid is selected from among hydrochloric acid, sulfuric acid, phosphoric acid, citric acid and tartaric acid.

3. Ready-to-use agent for oxidative coloring of keratin fibers which is prepared by mixing a dye carrier composition with an oxidant just before use and is characterized in that the dye carrier composition contains at least one compound of formula (I) as defined in claim 1.

4. Agent as defined in claim 3, characterized in that it contains the compound of formula (I) in an amount from 0.01 to 10 weight percent (based on the dye carrier composition).

5. Agent as defined in claim 3, characterized in that it contains at least one developer.

6. Agent as defined in claim 3, characterized in that additionally it contains other developers and/or couplers and/or direct dyes.

7. Agent as defined in claim 5, characterized in that the total amount of developers and couplers is 0.01 to 10 weight percent (based on the dye carrier composition).

8. Agent as defined in claim 6, characterized in that the total amount of direct dyes is from 0.1 to 10 weight percent (based on the dye carrier composition).

9. Agent as defined in claim 3, characterized in that it is a hair colorant.

10. Method for preparing the compounds of formula (I) as defined in claim 1 whereby first 3,5-dinitrobenzoyl chloride is made to react with resorcinol under Friedel-Crafts conditions and the resulting product is then catalytically hydrogenated to give the end product of formula (I) which finally is isolated either as the free base or as the acid adduct.

* * * * *